United States Patent [19]

Ochiai et al.

[11] 4,008,227
[45] Feb. 15, 1977

[54] CEPHALOSPORINS
[75] Inventors: Michihiko Ochiai, Osaka; Osami Aki, Kawanishi; Akira Morimoto, Osaka; Taiiti Okada, Kyoto, all of Japan
[73] Assignee: Takeda Chemical Industries, Ltd., Japan
[22] Filed: June 25, 1974
[21] Appl. No.: 483,083
[30] Foreign Application Priority Data
  June 25, 1973 Japan .............................. 48-71526
  Aug. 18, 1973 Japan .............................. 48-92677
[52] U.S. Cl. ........................... 260/243 C; 424/246
[51] Int. Cl.² ....................................... C07D 501/36
[58] Field of Search ............................. 260/243 C
[56] References Cited
UNITED STATES PATENTS

| | | | |
|---|---|---|---|
| 3,855,213 | 12/1974 | Dunn et al. | 260/243 C |
| 3,878,204 | 4/1975 | Ochiai et al. | 260/243 C |
| 3,890,309 | 6/1975 | Ochiai et al. | 260/243 C |
| 3,892,737 | 7/1975 | Ochiai et al. | 260/243 C |

FOREIGN PATENTS OR APPLICATIONS 2,162,575   7/1972   Germany ...................... 260/243 C OTHER PUBLICATIONS
Culvenor, (Amine Oxides), Reviews of Pure and Applied Chemistry, vol. 3 (1953) pp. 83–86 and 110.

*Primary Examiner*—Paul M. Coughlan, Jr.
*Attorney, Agent, or Firm*—Craig & Antonelli

[57] ABSTRACT

A compound of the formula:

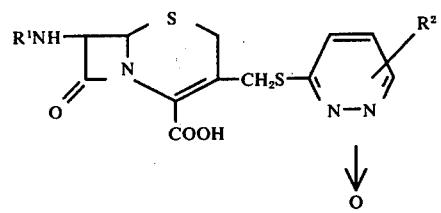

wherein $R^1$ represents mandeloyl or 2-(3-sydnone)-acetyl group and $R^2$ represents a hydrogen atom, a halogen, an alkyl or an alkoxyl group, or a pharmaceutically accetable salt thereof, is found to have a broad antimicrobial spectrum and, in particular, effective against gram-negative bacteria as well as gram-positive ones. Examples thereof include 7-[D-(−)-mandelamido]-3-[6'-(3'-methylpyridazinyl)-thio-methyl]-3-cephem-4-carboxylic acid 2'-oxide, 7-[D-(−)-mandelamido]-3-[6'-(3'-methoxypyridazinyl)-thiomethyl]-3-cephem-4-carboxylic acid 1'-oxide, and 7-[2'-(3'-sydnone)acetamido]-3-[6''-(3''-methylpyridazinyl)-thiomethyl]-3-cephem-4-carboxylic acid 2''-oxide.

17 Claims, No Drawings

CEPHALOSPORINS

This invention relates to novel cephalosporins and preparation thereof. More particularly, this invention relates to cephalosporins of the formula:

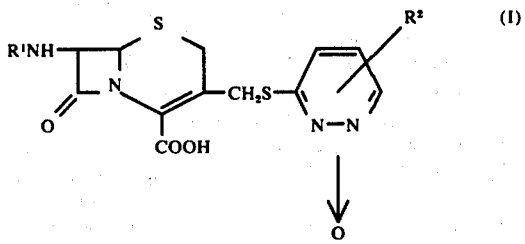

wherein $R^1$ represents a mandeloyl or 2-(3-sydnone)-acetyl group and $R^2$ represents a hydrogen atom, a halogen, an alkyl or an alkoxy group, or a pharmaceutically acceptable salt thereof and also relates to processes for producing the same.

Heretofore, studies on synthetic cephalosporin derivatives have been directed to the conversion of 7-aminocephalosporanic acid to various acyl derivatives at the 7-position or to derivatives at the 3-acetoxy group in order to synthesize compounds having either a broad anitbacterial spectrum or a specific antibacterial spectrum. However, these well-known cephalosporin derivatives are not yet satisfactory in antimicrobial activities against a wide variety of microorganisms. Hence, a compound has been sought after which has a broad antimicrobial spectrum and is effective even at a lower concentration.

It has now been found that novel cephalosporins represented by the above formula (I) have broader antimicrobial spectra as compared with those of known cephalosporins. For example, the cephalosporin compounds (I) are effective against colitics germs (*Escherichia coli*), *Proteus morganii*, etc. at a remarkably low concentration, while commercially available cephalosporins are not. In addition, it has been discovered that the cephalosporins (I) are also effective against various pathogenic bacteria at a lower concentration than that of known cephalosporins.

In the cephalosporins (I), $R^2$ represents a hydrogen atom, a halogen such as chlorine, bromine or the like, an alkyl group such as methyl, ethyl, propyl or the like, or an alkoxy group such as methoxy, ethoxy, propyloxy (propoxy), butyloxy, octyloxy or the like, while the oxide group is such that the oxygen atom is attached to either one of the N atoms of the pyridazine nucleus.

The cephalosporins (I) can be used as it is, namely with a free carboxyl group at the 4-position or, alternatively, may be used as salts with nontoxic cations such as sodium, potassium, etc., basic amino acids such as arginine, ornithine, lysine, histidine, etc. or polyhydroxyalkylamines such as N-methylglucamine, diethanolamine, triethanolamine, trishydroxymethylaminomethane, etc. Further, it is possible to esterify the 4-carboxyl groups of these derivatives to obtain biologically active ester derivatives which, for instance, make for increased blood levels and sustained efficacy.

The cephalosporins (I) may be prepared, for example, by reacting a pyridazine-thiol N-oxide compound of the formula;

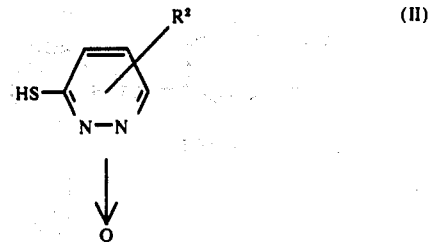

wherein $R^2$ is as previously defined, or a salt thereof, with a cephalosporanic acid compound of the formula;

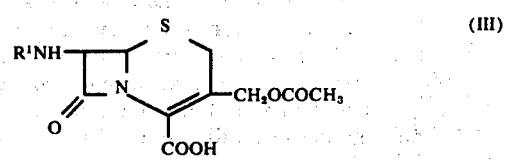

wherein $R^1$ has the same meanings as above, or a salt thereof. These starting compounds (II) and (III) can be reacted each in such forms as the free compound or a salt with an alkali or alkaline earth metal such as sodium, potassium, calcium or the like or with an organic amine such as triethylamine, dimethylaniline, picoline or the like.

This reaction is desirably conducted in a solvent. For example, use can be made of water, heavy water or organic solvents readily miscible with water and inert to the starting compounds, such as dimethylformamide, dimethylacetamide, dioxane, acetone, alcohol, acetonitrile, dimethylsulfoxide, tetrahydrofuran, etc. The reaction temperature and time depend, among other factors, upon the starting compounds, solvent and catalyst, to be employed but generally the reaction is carried out at a selected temperature within the range of 0° to 100° C for a selected time of a few hours to several days. The reaction is desirably conducted in the neighborhood of neutrality or between pH 2 and 8 and, for better results, between pH 5 and 8. To prevent oxidation of the thiol compound, i.e. pyridazine-thiol N-oxide (II), it is advantageous to carry out the reaction in an inert gaseous atmosphere, e.g. nitrogen gas. When a cephalosporanic acid compound (III) wherein $R^1$ is mandeloyl group is employed as the starting compound, the hydroxy group of the said mandeloyl group may be protected with an easily removable group, e.g. various acyl groups such as formyl, dichloroacetyl, trichloroacetyl, etc., tetrahydropyranyl, β,β,β-trichloroethoxycarbonyl, benzyl, etc. Such protecting groups can be removed with ease under mild conditions which will not interfere with the cephem ring, for example by hydrolysis with use of a mild acid or alkali or an esterase, by catalytic or other chemical reduction or by reduction with a microorganism.

The cephalosporin compounds (I) can also be produced by reacting a 7-aminocephalosporanic acid compound of the formula;

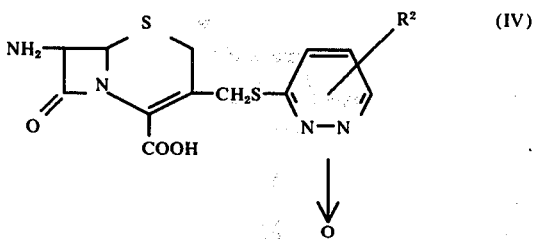

wherein $R^2$ has the same meanings as above, or a salt or ester thereof, with a carboxylic acid compound of the formula;

$$R^1OH \qquad (V)$$

wherein $R^1$ has the same meanings as above, or a derivative thereof. In conducting this reaction, the 4-carboxyl group of 7-amino compound (IV) may be in any forms that can be easily converted into a free carboxyl group by treatment with an alkali, acid or enzyme or by reduction, or in the form of an ester which is active in vivo. Thus, the corresponding salts with alkali metals, alkaline earth metals, organic amines, etc., e.g. sodium, potassium, magnesium, calcium, aluminum, triethylamine, etc., and the corresponding esters with $\beta$-methylsulfonylethyl, trimethylsilyl, dimethylsilenyl, benzhydryl, $\beta,\beta,\beta$-trichloroethyl, phenacyl, p-methoxybenzyl, p-nitrobenzyl, methoxymethyl, etc. may be mentioned. The carboxylic acid compound (V) can be used in the acylation reaction as the free acid or as the corresponding salt with sodium, potassium, calcium, trimethylamine, pyridine or the like or, further, as reactive derivatives such as acid halide, acid anhydride, mixed acid anhydride, cyclic carboxy-anhydride, active amide, ester, etc. (among which the acid chloride, alkyl carbonate anhydride, aliphatic carboxylic acid anhydride, acid azolide, etc. are more commonly employed). When the carboxylic acid compound (V) is employed in the form of free acid or salt, a suitable condensing agent is used together. The condensing agent includes, among others, di-substituted carbodiimides, (e.g. N,N'-dicyclohexylcarbodiimide), azolide compounds (e.g. N,N'-carbonylimidazole, N,N'-thionyldiimidazole, etc.), and such dehydrating agents as N-ethoxycarbonyl-2-ethoxy-1,2-dihydroquinoline, phosphorus oxychloride, alkoxy-acetylene, etc. It appears that when such a condensing agent is employed, the reaction proceeds via a reactive derivative at the carboxyl function.

This reaction can be conducted advantageously and smoothly in the presence of a solvent. As said solvent, use may be made of the common solvents and their mixtures unless such solvents do not interfere with the present reaction. There may be mentioned, therefore, such solvents as water, acetone, tetrahydrofuran, dioxane, acetonitrile, chloroform, dichloromethane, dichloroethylene, pyridine, dimethylaniline, dimethylsulfoxide, etc. may be mentioned. While the reaction temperature is virtually optional, the reaction usually is carried out under cooling or at room temperature.

The reaction of 7-aminocephalosporanic acid compound (IV) with carboxylic acid derivative (V) can be conducted in the presence of a culture, either as it is or after suitable processing, of a bacterial strain belonging to any of the genera Escherichia, Bacillus, Proteus or Pseudomonas. For this purpose, mandelic acid derivative can also be used, aside from the free compound and salts, in such forms as amino acid derivatives, e.g. N-mandeloylglycine, thioglycolic acid derivative, amide and alkyl esters. Among the bacteria which can be employed for this purpose are *Escherichia coli* IFO-3542, *Escherichia coli* ATCC-9637, *Escherichia coli* var. communior IFO-3547, *Escherichia coli* var. communior IFO-3548, *Bacillus* sp. ATCC-14552, *Proteus rettgeri* ATCC-9250, *Escherichia coli* IFO-13502 (FERM-P-1718), *Escherichia coli* IFO-3470 (FERM-P-1720), *Escherichia coli* IFO-3450 (FERM-P-1719), *Pseudomonas putida* IFO-3537 (FERM-P-1717), *Bacillus* sp. IFO-12063 (FERM-P-1716), etc.

The enzymatic acylation reaction is ordinarily carried out by contacting e.g. any of the following (1) through (4) with 7-aminocephalosporanic acid compound (IV) and carboxylic acid compound (V). Thus, any of the above-mentioned bacterial strains is first cultivated and the resultant culture is used as it is or after suitable processing.

In the latter instance, when said synthesizing activity occurs intracellularly, (1) the cells harvested from the culture broth, (2) a cell-free extract containing the cephalosporin ester-synthesizing enzyme which can be obtained from said cells by any known procedure, (3) a partially or thoroughly purified cephalosporin ester-synthesizing enzyme which can be obtained from said cell-free extract by any known procedure and (4) a cephalosporin ester-synthesizing enzyme derivative prepared by attaching said partially or thoroughly purified enzyme to a water-insoluble macromolecular substance by physical or chemical means, among others, can be successfully employed. On the other hand, when said synthesizing activity occurs extracellularly, there may be employed (1) the supernatant fluid obtainable following the removal of cells from the cultrue broth, (2) a partially or thoroughly purified cephalosporin ester-synthesizing activity which can be obtained from the supernatant by any known procedure and (3) said cephalosporin ester-synthesizing activity as attached either physically or chemically to a water-insoluble macromolecular substance, to name but a few examples. In these instances, the condensation reaction ordinarily is desirably conducted in an aqueous solution, with the pH of the reaction mixture being preferably controlled within the range of 4 to 8 and, for still better results, between 4.5 and 6.5. When the culture broth or processed broth is water-soluble, the above condensation reaction is performed in a genuine solution but when said broth or processed broth is water-insoluble, the same reaction is carried out in suspension or, alternatively, by filling a column with the water-insoluble cephalosporin ester-synthesizing enzyme derivative and passing an aqueous solution of carboxylic acid compound (V) and 7-amino cephalosporanic acid compound (IV) through the column so that the condensation reaction may take place as the solution flows down the column.

In these instances, a water-soluble organic solvent such as an alcohol or acetone may be added to the reaction mixture to enhance the yield of condensation. While the reaction time depends upon such factors as the concentration of substrate compounds, the potency of the cephalosporin ester-synthesizing enzyme and the reaction temperature, it is ordinarily within the range of 10 minutes to 300 minutes or longer. The reaction temperature is selected from within the range of 5° to 50° C. The concentrations of substrates are primarily determined by reference to the potency of cephalosporin ester-synthesizing activity and, ordinarily, the concentration of 7-aminocephalosporanic acid compound (IV) is selected from within the range of 0.1 to 20 percent by weight. To attain a high production yield of cephalosporin (I), it is desirable at least to employ one molecular equivalent of carboxylic acid compound (V) with respect to 7-aminocephalosporanic acid compound (IV).

As a cultural method for the production of said culture broth, any of aerated stirring culture, shake culture and stational culture may be employed, although aerobic culture is generally preferred. The culture medium may comprise one or, in combination, two or more of such natural ingredients as meat extract, yeast extract, peptone, casamino acid, corn steep liquor, etc., and may be supplemented, as necessary, with 0.05 to 0.5 percent of phenylacetic acid and, in adequate amounts, carbohydrates, organic acids, various carbon compounds such as normal paraffins, various inorganic and organic nitrogenous compounds including nitrogen in amino- or nitrate-form, metallic ions such as phosphates, magnesium salts, sodium chloride, etc. and various vitamins. The medium is adjusted to pH 6 to pH 9 before use. While the cultivation time varies with such other conditions as the particular strain of bacterium used and other cultural conditions, e.g. the cultural equipment, composition of medium and cultivation temperature, in particular, it is advisable to suspend the cultivation when the cephalosporin ester-synthesizing activity of the broth has reached a peak which lies somewhere between the second half of the logarithmic phase of growth and the first half of the stationary phase of growth of the bacterium. Ordinarily, a time of 8 to 48 hours is adequate.

The 7-aminocephalosporanic acid compound (IV) mentioned above can be conveniently obtained generally by permitting pyridazine-thiol N-oxide compound (II) to act upon, for example, cephalosporin C from a fermentation process and deacylating the resultant 3-pyridazinylthiomethyl compound in a conventional manner. Of the various deacrylating methods heretofore known, particularly advantageous is the imidohalide process which comprises reacting the same compound with a haloimidating agent such as phosphorus pentachloride in the presence of an acid acceptor, reacting the resultant imido-halide compound with alcohol and finally hydrolyzing the resultant iminoether compound. Alternatively, in the above imido-halide process, one may react said imino-halide compound with a sulfur compound such as thioacetamide, hydrogen sulfide, sodium sulfide, sodium hydrosulfide, methylmercaptan, sodium methylmercaptan, thioacetic acid, potassium thioacetate or the like, or react the cephalosporin C derivative with a sulfidizing agent such as phosphorus pentasulfide, or when the free thiol compound has been obtained, react it further with an alkylating agent and an acylating agent to obtain the iminothioether compound and, then, subject it to solvolysis and, then, to hydrolysis. In this connection, the contemplated cephalosporin (I) can also be directly obtained by reacting said carboxylic acid compound derivative such as mandelic acid halide with any of the iminohalide compound, iminoether compound and iminothioether compound which are obtainable as intermediates in said deacylation procedures.

When $R^1$ of the carboxylic acid compound (V) is mandeloyl group, the $\alpha$-hydroxyl group is desirably protected by a suitable protecting group, and such protecting group can be removed after the reaction. The protecting group must be removed under mild conditions which will not be unfavorable to the objective compound (I). Thus, the protecting group is desirably a group which will leave a hydroxyl group without affecting the cephem ring and other moieties in any manner. By way of example, it is one that can be converted to a hydroxyl group by hydrolysis under netural conditions with a mild acid or alkali or an esterase, by catalytic or other chemical reduction or by reduction with a mircroorganism. Therefore, said protective group on hydroxyl may more commonly be any of such acyl groups as dichloroacetyl, trichloroacetyl, etc., tetrahydropyranyl, $\beta,\beta,\beta$-trichloroethoxycarbonyl, benzyl, such silyl groups as trimethoxysilyl, etc., $\beta$-methylsulfonylethyl, etc. Of these groups, certain groups such as formyl, dichloroacetyl, trichloroacetyl, etc. can be removed under weakly alkaline conditions. For example, by allowing the compound to stand in a few to 10 percent aqueous solution of sodium hydrogen carbonate at 0° C to room temperature for 1 to serveral hours, these groups can be completely and safely removed. The tetrahydropyranyl group can be removed under acid conditions. Ordinarily, such agents as trifluoroacetic acid or acetic acid containing hydrogen chloride, for instance, are employed. In these instances, too, the protective groups can be removed at 0° C to room temperature within 1 hour to several hours. Certain groups such as $\beta,\beta,\beta$-trichloroethoxycarbonyl can be removed by reduction, for example by treatment with zinc dust in the presence of acetic acid, formic acid or the like.

While mandelic acid compounds among the carboxylic acid compound (V) may occur as D- and L-isomers with respect to the $\alpha$-carbon, whichever of these isomers, as well as their mixture, can be successfully employed for the purposes of this invention. It is known that generally, of cephalosporins having a center of asymmetry at $\alpha$-position, D-isomers are more antibiotic than the L-isomers.

According to its properties, the contemplated compound thus produced can be purified by such procedures as column chromatography, extraction, precipitation, countercurrent distribution, recrystallization, etc.

Further, it is possible to esterify the 4-carboxyl groups of these compounds to obtain biologically active ester derivatives which, for instance, make for increased blood levels and sustained efficacy.

Besides being completely new, these cephalosporin (I) have excellent antibiotic characteristics. For example, these compounds are highly active against a broad spectrum of pathogenic bacteria, including gram-positive, gram-negative and penicillin-resistant bacteria, and can be used in such dosage forms as injections, capsules, etc. just as the conventional cephalosporin preparations. Of the compounds according to this invention, 7-[2'-(3'-sydnone)acetamido]-3-[6''-(3''-methylpyridazinyl)-thiomethyl]-3-cephem-4-carboxylic acid 2''-oxide and 7$\beta$-mandelamino-3-[6''-(3''-methylpyridazinylthiomethyl)]-3-cephem-4-carboxylic acid 1''-oxide, for instance, are normally injected subcutaneously as an aqueous solution of the sodium salts containing 0.25 to 1 gram daily for adult humans.

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g.", "mg.", "ml.", "cm.", "ppm", "cps", "r.p.m.", "M", "mM", "mcg" and "decomp." are abbreviations of "gram", "milligram", "milliliter", "centimeter", "part per million", "cycles per second", "revolutions per minute", "Mole", "milli-Mole", "microgram" and "decomposed", respectively; all the temperatures are uncorrected and the percentages are all on the weight basis except specifically defined.

EXAMPLE 1

In 10 ml. of water are dissolved 1 g. of sodium 7-[D-(—)-mandelamido]cephalosporanate and 420 mg. of sodium hydrogen carbonate, and then 249 mg. of 3-methyl-6-pyridazine-thiol 2-oxide. The mixture is stirred at 57° C for 10 hours. After cooling, the reaction mixture is run onto a column of polystyrene resin (Amberlite XAD-II, trade name of Rohm & Haas Co.) and eluted with water. The eluate is lyophilized to obtain 458 mg. of 7-[D-(—)-mandelamido]-3-[6'-(3'-methylpyridazinyl)thiomethyl]-3-cephem-4-carboxylic acid 2'-oxide sodium salt. Melting point 196° – 198° C (decomp.).

Elemental analysis, calculated for $C_{21}H_{19}O_6N_4S_2Na.3/2$ $H_2O$;

C, 46.92; H, 4.13; N, 10.25

Found

C, 47.29; H, 4.01; N, 9.79

The infrared absorption spectrum (KBr disc) of this product shows an absorption of the $\beta$-lactam at 1761 $cm^{-1}$ and the nuclear magnetic resonance spectrum (in $D_2O$, 100 Mc.) of the same product shows a singlet of pyridazine ring methyl protons at 2.44 ppm and doublets (J=5 cps) or protons at 6- and 7-positions at 5.03 and 5.61 ppm, respectively.

| MIC (mcg./ml.) | | |
|---|---|---|
| Staphylococcus aureus | 209P | 0.1 |
| " | No. 87 | 5 |
| Bucillus subtilis | PCI 219 | <0.01 |
| Sarcina lutea | PCI 1001 | 0.2 |
| Escherichia coli | NIHJ | 0.5 |
| Proteus vulgaris | Eb51 | 1 |
| Proteus mirabilis | Eb59 | 5 |

EXAMPLE 2

In 10 ml. of water are dissolved 1 g. of sodium 7-[D-(—)-mandelamido]cephalosporanate and 485 mg. of 3-methoxy-6-pyridazine-thiol 1-oxide sodium salt, and the solution is stirred at 58° – 60° C for 11 hours. After cooling, the reaction mixture is run onto a column of polystyrene resin (Amberlite XAD-II) and eluted with 3% ethanol. The eluate is lyophilized to obtain 201 mg. of 7-[D-(—)-mandelamido]-3-[6'-(3'-methoxypyridazinyl) thiomethyl]-3-cephem-4-carboxylic acid 1'-oxide sodium salt. Melting point 170° – 177° C (decomp.). The infrared absorption spectrum of this product shows an absorption of the $\beta$-lactam at 1765 $cm^{-1}$.

Elemental analysis, calculated for $C_{21}H_{19}O_7N_4S_2.Na.H_2O$;

C, 46.32; H, 3.89; N, 10.29

Found

C, 46.53; H, 4.35; N, 9.82

EXAMPLE 3

In 10 ml. of water are dissolved 2.23 g. of sodium 7-[D-(—)-mandelamido]cephalosporanate, 704 mg. of 6-pyridazine-thiol 2-oxide and 504 mg. of sodium hydrogen carbonate, and the solution is stirred at 57° – 59° C for 10 hours. Thereafter, the reaction mixture is treated in the similar manner as Example 1 to obtain 7-[D-(—)-mandelamido]-3-[6'-(pyridazinyl) thiomethyl]-3-cephem-4-carboxylic acid 2'-oxide sodium salt; 378 mg.

EXAMPLE 4

In 12 ml. of water are dissolved 2.23 g. of sodium 7-[D-(—)-mandelamido]cephalosporanate, 1.0 g. of 3-chloro-6-pyridazine-thiol 1-oxide and 420 mg. of sodium hydrogen carbonate. The solution is stirred and the reaction mixture is treated in a similar manner to Example 2 to obtain 403 mg. of 7-[D-(—)-mandelamido]-3-[6'-(3'-chloropyridazinyl)thiomethyl]-3-cephem-4-carboxylic acid 1'-oxide sodium salt.

Elemental analysis, calculated for $C_{20}H_{16}O_6N_4S_2ClNa.2$ $1/2 H_2O$;

C, 41.70; H, 3.68; N, 9.73

Found

C, 41.68; H, 3.72; N, 9.60

EXAMPLE 5

In 15 ml. of water are dissolved 2.23 g. of sodium 7-[D-(—)-mandelamido]cephalosporanate, 1.04 g. of 3-bromo-6-pyridazine-thiol 1-oxide and 420 mg. of sodium hydrogen carbonate. The solution is treated in a similar manner to Example 2 to obtain 421 mg. of 7-[D-(—)-mandelamido]-3-[6''-(3'-bromopyridazinyl)-thiomethyl]-3-cephem-4-carboxylic acid 1'-oxide sodium salt.

EXAMPLE 6

In a mixture of 100 ml. water and 100 ml. of acetone is dissolved 5 g. of sodium hydrogen carbonate, and then 3.7 g. of 7-amino-3-[6''-(3'-methoxypyridazinyl)-thiomethyl]-3-cephem-4-carboxylic acid 1'-oxide. The mixture is stirred under cooling with ice. To this mixture is added a solution of 2.2 g. of O-formylmandelylchloride in 40 ml. of acetone and the mixture is stirred at 0° C for 1 hour and, then, at room temperature for 2 hours. After the reaction has been completed, most of the acetone is distilled off under reduced pressure and the residue is washed with ether. The aqueous layer is then adjusted to pH 2 with dilute hydrochloric acid and the resultant precipitate is collected by filtration.

This product is crude 7-(O-formylmandelamido)-3-[6'-(3'-methoxypyridazinyl)thiomethyl]-3-cephem-4-carboxylic acid 1'-oxide. It is dissolved in 100 ml. of a 10% aqueous solution of sodium hydrogen carbonate and the solution is stirred at room temperature for 3 hours.

The solution is then run onto a column of polystyrene resin and eluted with water. The eluate is lyophilized to obtain 1.5 g. of 7-[D-(—)-mandelamido]-3-[6'-(3'-methoxypyridazinyl)thiomethyl]-3-cephem-4-carboxylic acid 1'-oxide sodium salt. This product agrees completely with the product obtained in Example 2.

| MIC (mcg./ml.) | | |
|---|---|---|
| Staphylococcus aureus | 209P | <0.78 |
| " | 1840 | 1.56 |
| Escherichia coli | NIHJ | 1.56 |

| | | |
|---|---|---|
| -continued | | |
| Klebsiella pneumoniae | | 1.56 |

EXAMPLE 7

In 40 ml. of dry tetrahydrofuran are dissolved 2.36 g. of O-tetrahydropyranylmandelic acid and 1.01 g. of triethylamine and, then, 1.36 g. of isobutyl chloroformate is added at −10° C, followed by stirring for 20 minutes. Separately, 35 ml. of an aqueous solution containing 1.01 g. of triethylamine and 3.74 g. of 7-amino-3-[6'-(3'-chloropyridazinyl)thiomethyl]-3-cephem-4-carboxylic acid 1'-oxide is prepared. The solution is mixed with the previously prepared solution and the mixture is stirred at 5° C for 1 hour and, then, at room temperature for 1 hour. Then, the tetrahydrofuran is distilled off under reduced pressure and 20 ml. of water and 100 ml. of ethyl acetate are added to the residue. The mixture is adjusted to pH 3.0 with 10% dilute hydrochloric acid, shaken and separated into two layers. The ethyl acetate layer is washed with water, dried and concentrated under reduced pressure. To the residue is added 20 ml. of trifluoroacetic acid. After stirring for 30 minutes, 100 ml. of dry ether is added to the mixture and the resultant precipitate is collected by filtration. The product is dissolved in 20 ml. of a 5% aqueous solution of sodium hydrogen carbonate and the solution is run onto a column of polystyrene resin and eluted with 5% ethanol. The eluate is lyophilized to obtain 1.2 g. of 7-[D-(−)-mandelamido]-3-[6'-(3'-chloropyridazinyl)thiomethyl]-3-cephem-4-carboxylic acid 1'-oxide sodium salt. This product agrees completely with the product obtained according to Example 4.

| MIC (mcg./ml.) | | |
|---|---|---|
| Staphylococcus aureus | 209P | <0.78 |
| " | 1840 | <1.56 |
| Escherichia coli | NIHJ | 1.56 |
| Klebsiella pneumoniae | | <0.78 |
| Proteus vulgaris | | 3.125 |
| Proteus morganii | Eb53 | 25 |

EXAMPLE 8

In a mixture of 45 ml. water and 25 ml. acetone are dissolved 1.77 g. of 7-amino-3-['-(3'-methylpyridazinyl)thiomethyl]-3-cephem-4-carboxylic acid 2'-oxide and 1.35 g. of sodium hydrogen carbonate. Under cooling with ice bath and stirring, 1 g. of the cyclic carboxyanhydride prepared from D-(−)-mandelic acid and phosgene is added in small portions. After the addition has been completed, the ice bath is removed and the mixture is stirred for 3 hours. The reaction mixture is washed twice with ether and adjusted to pH 3 with dilute hydrochloric acid. The precipitate is collected by filtration and dissolved in 15 ml. of a 5% aqueous solution of sodium hydrogen carbonate. This solution is run onto a column of polystyrene resin and elution is carried out with water. The eluate is lyophilized to obtain 835 mg. of 7-[D-(−)-mandelamido]-3-[6'-(3'-methylpyridazinyl)-thiomethyl]-3-cephem-4-carboxylic acid 2'-oxide sodium salt.

This product has been found to agree completely with the product obtained according to Example 1.

EXAMPLE 9

The cells of Escherichia coli IFO-13502 from four slant cultures (medium A, 2% agar) obtained after an incubation time of 24 hours at 28° C are suspended in 40 ml. of physiological saline and 10 ml. aliquots of the suspension are inoculated into 2-liter Sakaguchi's flasks containing 500 ml. of medium B. The flasks are incubated under shaking at 24° C for 24 hours to prepare a seed culture. The two-liter seed culture is then inoculated into 100 liters of medium B (containing 0.005% of Antifroth F 102) in a fermentation tank of 200-liter capacity and aerated-stirring-culture is carried out at 50% aeration, 150 r.p.m. and 24° C for 24 hours. After the cultivation, the moist cells are collected by a Sharpless centrifuge and suspended in 5 liters of pure water. After the cells have been washed well, the suspension is centrifuged a second time to harvest about 1100 g. of washed moist cells. The washed cells are suspended in 10 ml. of 0.5M citrate phosphate buffer to 10 times the concentration of the culture broth and 10 ml. of a similar buffer containing 160 mM of mandelglycine and 80 mM of 7-amino-3-[6'-(3'-methylpyridazinyl)thiomethyl]-4-methoxymethoxycarbonyl-3-cephem-2'-oxide is added. Under stirring, the mixture is stirred at 37° C for 4 hours, by the end of which time 22mM of 7-(mandelamido)-3-[6'-(3'-methylpyridazinyl)thiomethyl]-4-methoxymethoxycarbonyl-3-cephem-2'-oxide has accumulated in the reaction system (by quantitative polarimetry).

This product is isolated and added to 50 ml. of trifluoroacetic acid under cooling with ice. The mixture is stirred for 1 hour, after which time dry ether is added. The precipitate is recovered by filtration and dissolved in a 5% aqueous solution of sodium hydrogen carbonate. The solution is run onto a column of polystyrene resin and eluted with water to obtain 2.1 g. of 7-(mandelamido)-3-[6'-(3'-methylpyridazinyl)thiomethyl]-3-cephem-4-carboxylic acid 2'-oxide sodium salt. This product has been found to agree completely with the product obtained according to Example 1.

| (note) (Medium A) | Meat extract | 10 g. |
|---|---|---|
| | Peptone | 10 g. |
| | NaCl | 5 g. |
| | Tap water | 1 l., pH 7.0 |

EXAMPLE 10

The washed cells of Escherichia coli IFO-13502 prepared in the same manner as Example 9 are suspended in 10 ml. of 0.5M citric acid phosphate buffer to ten times the concentration of the culture broth. To this suspension is added 10 ml. of a similar buffer containing 160 mM of mandelglycine and 80 mM of 7-amino-3-[6'-(3'-methoxypyridazinyl)thiomethyl]-4-methoxymethoxycarbonyl-3-cephem-1'-oxide. The mixture is stirred at 37° C for 4 hours, by the end of which time 27 mM of 7-(mandelamido)-3-[6'-(3'-methoxypyridazinyl)thiomethyl]-4-methoxymethoxycarbonyl-3-cephem-1'-oxide has accumulated (by quantitative polarimetry).

Thereafter, the reaction mixture is treated in the same manner as Example 9 to obtain 1.9 g. of 7-(mandelamido)-3-[6'-(3'-methylpyridazinyl)thiomethyl]-3-cephem-4-carboxylic acid-2'-oxide sodium salt.

| (note) (Medium B) | Sodium glutamate | 20 g. |
|---|---|---|
| | Yeast extract | 10 g. |
| | Phenylacetic acid | 2 g. |
| | NaCl | 2 g. |
| | $KH_2PO_4$ | 1 g. |
| | $MgSO_4 \cdot 7H_2O$ | 0.2 g. |
| | Tap water | 1 l., pH 7.0 |

EXAMPLE 11

In 25 ml. of methylene chloride is suspended 500 mg. of 2-(3-sydnone)acetic acid, followed by the addition of 1.0 g. of phosphorus pentachloride. The mixture is stirred at room temperature for 30 minutes to prepare a solution of 2-(3-sydnone)acetyl chloride. Meanwhile, in a mixture of 10 ml. water and 15 ml. ethyl acetate are dissolved 1.24 g. of 7-amino-3-[6'-(3'-methylpyridazinyl)thiomethyl]-3-cephem-4-carboxylic acid 2'-oxide and 3.0 g. of sodium hydrogen carbonate. While the solution is ice-cooled, the methylene chloride solution prepared above is added. The mixture is stirred at 0° C for 30 minutes and, then, at room temperature for 2 hours, after which time the organic solvent is distilled off at room temperature under reduced pressure. The residue is washed with 10 ml. of ethyl acetate and the aqueous layer is adjusted to pH 2.5 with dilute hydrochloric acid. The precipitate is collected by filtration, washed with water and dried. The described procedure yields 1.09 g. of crude 7-[2'-(3'-sydnone)acetamido]-3-[6''-(3''-methylpyridazinyl)thiomethyl]-3-cephem-4-carboxylic acid 2''-oxide. This product is dissolved in a 5% aqueous solution of sodium hydrogen carbonate and separated and purified on a column of Amberlite XAD-2. The product is lyophilized to obtain the corresponding sodium salt. This product melts at 197° – 198° C (decomp.) and gives the following analysis.

Elemental analysis, calculated for $C_{17}H_{15}O_7N_6S_2Na \cdot 3\frac{1}{2} H_2O$;

C, 36.11; H, 3.92; N, 14.86
Found
C, 36.42; H, 3.80; N, 14.32

The infrared absorption spectrum (KBr disc) of this product shows an absorption for the β-lactam at 1740 cm$^{-1}$. The nuclear magnetic resonance spectrum of the same (in $D_2O$, 100 Mc) shows a singlet assignable to the pyridazine methyl protons at 2.53 ppm and doublets (J=5 cps) assignable to protons in 6- and 7-positions at 5.19 ppm and 5.75 ppm, respectively.

| MIC (mcg./ml.) | | |
|---|---|---|
| Staphylococcus aureus | 209P | <0.78 |
| " | 1840 | 1.56 |
| Escherichia coli | NIHJ | 1.56 |
| Klebsiella pneumoniae | | 1.56 |

EXAMPLE 12

In 10 ml. of water are dissolved 701 mg. of sodium 7-[2'-(3'-sydnone)acetamido]cephalosporanate and 351 mg. of 3-chloro-6-pyridazine-thiol 1-oxide sodium salt, and the reaction is allowed to take place at 60° C for 5 hours, with stirring. The reaction product is run onto a column of Amberlite XAD-2 and eluted with water. The eluate is lyophilized to obtain 86 mg. of 7-[2'-(3'-sydnone)acetamido]-3[6''-(3''-chloropyridazinyl)-thiomethyl]-3-cephem-4-carboxylic acid 1''-oxide sodium salt.

This product melts at 119° – 135° C (decomp.) and gives the following analysis.

Elemental analysis, calculated for $C_{16}H_{12}O_7N_6S_2ClNa \cdot 3\frac{1}{2} H_2O$;

C, 32.80; H, 3.27; N, 14.34
Found
C, 33.12; H, 2.83; N, 13.55

The nuclear magnetic resonance spectrum of the above product (in $D_2O$, 100 Mc.) shows a doublet (J=5 cps) assignable to protons in the 6- and 7-positions at 5.19 and 5.76 ppm, respectively, a singlet of sydnoneacetic acid methylene protons at 5.50 ppm and a doublet (d=15 cps) of pyridazine ring protons at 7.64 – 8.11.

| MIC (mcg./ml.) | | |
|---|---|---|
| Staphylococcus aureus | 209P | <0.78 |
| " | 1840 | 1.56 |
| Escherichia coli | NIHJ | 1.56 |
| Klebsiella pneumoniae | | 1.56 |

EXAMPLE 13

In 10 ml. of water are dissolved 703 mg. of sodium 7-[2'-(3'-sydnone)acetamido]cephalosporanate and 342 mg. of 3-methoxy-6-pyridazine-thiol 1-oxide sodium salt, and, under stirring, the solution is reacted at 60° C for 4 hours. The reaction mixture is run onto a column of Amberlite XAD-2 and eluted with water. The eluate is lyophilized to obtain 103 mg. of 7-[2'-(3'-sydnone)acetamido]-3-[6''-(3''-methoxypyridazinyl)-thiomethyl]-3-cephem-4-carboxylic acid 1''-oxide sodium salt. This product melts at 177° – 184° C (decomp.) and gives the following elemental analysis.

Elemental analysis, calculated for $C_{17}H_{15}O_8N_6S_2Na \cdot 2\frac{1}{2}H_2O$;

C, 36.23; H, 3.58; N, 14.91
Found
C, 36.28; H, 3.57; N, 14.47

| MIC (mcg./ml.) | | |
|---|---|---|
| Staphylococcus aureus | 209P | <0.78 |
| " | 1840 | 1.56 |
| Klebsiella pneumoniae | | 1.56 |

EXAMPLE 14

In 10 ml. of water are dissolved 438 mg. of sodium 7-[2'-(3'-sydnone)acetamido]cephalosporanate and 180 mg. of 3-methyl-6-pyridazine-thiol 2-oxide sodium salt, and, under stirring, the solution is reacted at 60° C for 50 hours.

The reaction product is run onto a column of Amberlite XAD-2 and eluted with water. The eluate is lyophilized to obtain 110 mg. of 7-[2'-(3'-sydnoneacetamido]-3-[6''-(3''-methylpyridazinyl)thiomethyl]-3-cephem-4-carboxylic acid 2''-oxide sodium salt.

This product agrees with the product obtained according to Example 11.

EXAMPLE 15

In 25 ml. of methylene chloride is suspended 500 mg. of 2-(3-sydnone)acetic acid, and 1.0 g. of phosphorus pentachloride is added. The mixture is stirred at room temperature for 35 minutes to prepare a solution of 2-(3-sydnone)acetyl chloride. Meanwhile, in a mixture of 10 ml. water and 10 ml. of acetone are dissolved 1134 mg. of 7-amino-3-[6'-(3'-chloropyridazinyl)thiomethyl]-3-cephem-4-carboxylic acid 1'-oxide and 3.0 g. of sodium hydrogen carbonate and while the solution is cooled with ice, the methylene chloride solution prepared previously is added.

Under stirring, the mixture is reacted at 0° C for 45 minutes and, then, at room temperature for 2.5 hours, after which the organic solvent is distilled off under reduced pressure at room temperature. The residue is washed twice with 10 ml. portions of ethyl acetate and the water layers are pooled and adjusted to pH 2.5 with dilute hydrochloric acid. The resultant precipitate is collected by filtration, washed with water and dried to obtain 935 mg. of crude 7-[2'-(3'-sydnone)acetamido]-3-[6''-(3''-chloropyridazinyl)thiomethyl]-3-cephem-4-carboxylic acid 1''-oxide. This product is dissolved in a 5% aqueous solution of sodium hydrogen carbonate and the solution is run onto a column of Amberlite XAD-2. Then, water is run through the column to obtain the sodium salt as a pure product. This product agrees with the product obtained according to Example 12.

EXAMPLE 16

In 10 ml. of dimethylacetamide is suspended 1111 mg. of 7-amino-3-[6'-(3'-methoxypyridazinyl)thiomethyl]-3-cephem-4-carboxylic acid 1'-oxide. Under cooling with ice, a methylene chloride solution of 2-(3-sydnone)acetic acid chloride prepared from 500 mg. of 2-(3-sydnone)acetic acid in a similar manner as described in Example 11 is added to the above suspension. The reaction mixture is stirred vigorously at 15°-20° C for 2 hours, after which the dimethylacetamide is distilled off under reduced pressure. The residue is dissolved in a 5% aqueous solution of sodium hydrogen carbonate under cooling with ice and, after washing with a small amount of ethyl acetate, the solution is run onto a column of Amberlite XAD-2. Then, water is run through the column to obtain 205 mg. of 7-[2'-(3'-sydnone)acetamido]-3-[6''-(3''-methoxy-pyridazinyl)thiomethyl]-3-cephem-4-carboxylic acid 1''-oxide sodium salt as a pure product. This product agrees with the product obtained according to Example 13.

What is claimed is:

1. A compound of the formula:

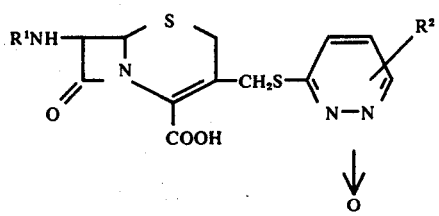

wherein $R^1$ represents mandeloyl or 2-(3-sydnone)-acetyl and $R^2$ represents hydrogen, chlorine, bromine, $C_1$-$C_3$ alkyl or $C_1$-$C_8$ alkoxy, or a pharmaceutically acceptable salt thereof.

2. A compound as claimed in claim 1, wherein $R^2$ represents hydrogen.

3. A compound according to claim 2, namely, 7-[D-(−)-mandelamido]-3-[6'-(pyridazinyl)thiomethyl]-3-cephem-4-carboxylic acid 2'-oxide.

4. A compound as claimed in claim 1, wherein $R^2$ represents alkyl.

5. A compound according to claim 4, namely, 7-[D-(−)-mandelamido]-3-[6'-(3'-methylpyridazinyl)thiomethyl]-3-cephem-4-carboxylic acid 2'-oxide.

6. A compound according to claim 4, namely, 7-[2'-(3'-sydnone)acetamido]-3-[6''-(3''-methylpyridazinyl)thiomethyl]-3-cephem-4-carboxylic acid 2''-oxide.

7. A compound as claimed in claim 1, wherein $R^2$ represents alkoxy.

8. A compound according to claim 7, namely, 7-[D-(−)-mandelamido]-3-[6'-(3'-methoxypyridazinyl)thiomethyl]-3-cephem-4-carboxylic acid 1'-oxide.

9. A compound according to claim 7, namely, 7-[2'-(3'-sydnone)-acetamido]-3-[6''-(3''-methoxypyridazinyl)-thiomethyl]-3-cephem-4-carboxylic acid 1''-oxide.

10. A compound as claimed in claim 1, wherein $R^2$ represents a halogen.

11. A compound according to claim 10, namely, 7-[D-(−)-mandelamido]-3-[6'-(3'-chloropyridazinyl)-thiomethyl]-3-cephem-4-carboxylic acid 1'-oxide.

12. A compound according to claim 10, namely, 7-[D-(−)-mandelamido]-3-[6'-(3'-bromopyridazinyl)-thiomethyl]-3-cephem-4-carboxylic acid 1'-oxide.

13. A compound according to claim 10, namely, 7-[2'-(3'-sydnone)acetamido]-3-[6''-(3''-chloropyridazinyl)-thiomethyl]-3-cephem-4-carboxylic acid 1''-oxide.

14. A compound as claimed in claim 1, wherein $R^2$ is chlorine, bromine, alkyl having 1-3 carbon atoms or alkoxy having 1-8 carbon atoms.

15. A compound as claimed in claim 14, wherein $R^2$ is selected from the group consisting of chlorine, bromine, methyl, ethyl, propyl, methoxy, ethoxy, propoxy, butyloxy and octyloxy.

16. A compound as claimed in claim 1, wherein said compound is in the form of the free carboxylic acid, sodium salt, potassium salt, arginine salt, ornithine salt, lysine salt, N-methylglucamine salt, diethanolamine salt, triethanolamine salt or trishydroxymethylaminomethane salt.

17. A compound as claimed in claim 1, wherein said compound is in the form of the free carboxylic acid.

* * * * *